(12) United States Patent
Castro et al.

(10) Patent No.: US 8,414,880 B2
(45) Date of Patent: *Apr. 9, 2013

(54) PDT TREATMENT METHOD FOR CELLULITES AND COSMETIC USE

(75) Inventors: Danilo Castro, Montevideo (UY); Wolfgang Neuberger, Labuan (MY)

(73) Assignee: Bioliter Pharme Marketing Ltd, F. T. Labuan (MY)

( * ) Notice: Subject to any disclaimer, the term of this patent is extended or adjusted under 35 U.S.C. 154(b) by 22 days.

This patent is subject to a terminal disclaimer.

(21) Appl. No.: 12/899,003

(22) Filed: Oct. 6, 2010

(65) Prior Publication Data

US 2011/0152745 A1     Jun. 23, 2011

Related U.S. Application Data

(63) Continuation-in-part of application No. 11/489,873, filed on Jul. 20, 2006, now abandoned.

(60) Provisional application No. 60/704,797, filed on Aug. 2, 2005.

(51) Int. Cl.
*A01N 63/00* (2006.01)

(52) U.S. Cl. ........ 424/93.1; 424/93.21; 604/20; 530/410

(58) Field of Classification Search .................... 604/20; 424/93.1; 514/410
See application file for complete search history.

(56) References Cited

U.S. PATENT DOCUMENTS

| | | | |
|---|---|---|---|
| 4,649,151 A | 3/1987 | Dougherty et al. | |
| 4,764,360 A * | 8/1988 | Malson | 424/10.32 |
| 5,776,074 A * | 7/1998 | Marzorati | 600/549 |
| 5,807,385 A | 9/1998 | Keller | |
| 6,074,666 A | 6/2000 | Desai et al. | |
| 6,120,987 A * | 9/2000 | Aspe | 435/4 |
| 6,206,873 B1 | 3/2001 | Paolini et al. | |
| 6,315,775 B1 * | 11/2001 | Thielen et al. | 606/16 |
| 6,605,080 B1 | 8/2003 | Altshuler et al. | |
| 6,743,215 B2 | 6/2004 | Bernabei | |
| 7,354,599 B2 | 4/2008 | Albrecht et al. | |
| 2001/0056294 A1 | 12/2001 | Hiramoto et al. | |
| 2002/0004053 A1 * | 1/2002 | Biel | 424/277.1 |
| 2004/0030369 A1 * | 2/2004 | Kubota | 607/89 |
| 2004/0232169 A1 * | 11/2004 | Glover et al. | 222/212 |
| 2005/0048287 A1 * | 3/2005 | Ebner et al. | 428/411.1 |
| 2005/0215524 A1 | 9/2005 | Albrecht et al. | |
| 2006/0019805 A1 * | 1/2006 | Heck | 482/121 |
| 2006/0035952 A1 | 2/2006 | Nifantiev et al. | |
| 2010/0184721 A1 * | 7/2010 | Choulot et al. | 514/54 |

FOREIGN PATENT DOCUMENTS

| | | |
|---|---|---|
| WO | 9948474 | 9/1999 |
| WO | 2005037372 | 4/2005 |

\* cited by examiner

*Primary Examiner* — Susan Hanley
(74) *Attorney, Agent, or Firm* — Bolesh J. Skutnik; B. J Associates

(57) ABSTRACT

Photosensitizer mixtures and method of treating cellulites by light illumination are presented. Photosensitizer is combined with cellular products, e.g. adipose cells, collagen, previously removed by liposuction. Concentrations used depend on treatment area, cellulite stage and whether cellulites are in depressed or elevated skin areas. The cosmetic treatment reduces/removes localized lipodystrophies, flaccidity, cellulite using localized laser, LED, etc emissions. Applied light energy destroys "fat" cells by a combination of chemical reactions primarily, and temperature, wherein cell walls break releasing cell fluid. Transmission devices guide radiation to the treatment site. One or more light sources like laser diodes or LEDs may be coupled into one or more optical fibers to increase the covered area and increase the amount of radiation in that area. Optical fibers can be introduced percutaneously or interstitially. Cell fluid in the treatment area is removed by a combination of techniques.

12 Claims, 5 Drawing Sheets

PDT TREATMENT METHOD FOR CELLULITES AND COSMETIC USE

CROSS-REFERENCE TO RELATED APPLICATIONS

This application is a continuation-in-part of U.S. patent application Ser. No. 11/489,873, filed Jul. 20, 2006 now abandoned, which claims the benefit of U.S. Provisional Application Ser. No. 60/704,797, filed Aug. 2, 2005, both of which are incorporated herein by reference.

FIELD OF THE INVENTION

The present invention relates to the field of cosmetic treatment and, in particular, relates to a photodynamic therapy (PDT) treatment to remove cellulite tissue and also excess adipose cells in areas of the body prone to buildup of such tissues.

BACKGROUND OF THE INVENTION

It is a well known fact that modern society has created an abundance of readily available foods, i.e., "fast foods," and also has created an environment where entertainment has fostered a sedentary life style of, for example, watching television, playing video games and talking on the phone while eating high caloric snack foods. This has allowed people to gain excess weight by an increase in adipose tissue. Certain heredity conditions have also created areas of excess fat cells that are difficult to remove in that they are in areas that are not affected or minimally affected by diet and exercise. In areas where fat cells have excessively accumulated, normally in the buttocks, hips, and thighs, especially in women, the collagen fibers are deformed, allowing pockets of fat cells to accumulate and deform the skin surface, producing bubbles or ripples, which are known as cellulite.

"Edematous-fibrosclerotic panniculopathy" is a medical term used to describe cellulite. Cellulite affects 80-90% of women in their post-pubertal period. Cellulite is found commonly on the hips, thighs, and buttocks giving a dimpled appearance in those areas of the body. It is not a disorder, but an issue of cosmetic concern to the individual. Cellulite is more often seen in women than in men due to the structural differences of their adipose tissue. Cellulite is not related to obesity or overweight, since it can occur even in normal and thin women.

Cellulite is different from the fat cell layer in the body. Most fatty deposits in an individual depend on his/her weight, life style and genetic makeup. The fat layer in the body has important functions, e.g., insulation, and protecting vital organs, etc. Cellulite is largely due to the structural conformation below the skin which appears as lumpy pockets of trapped fat giving uneven dimpling or orange peel skin.

Cellulite develops in the hypodermis or subcutaneous fat layer, where fat lobes are organized into chambers by surrounding strands of connective tissue. Below this layer is scarpus fascia in which fat cells enlarge when weight is gained. This layer is divided into chambers by connective tissue, which attaches the top layer of the skin to the lower layers of muscle. When these connective tissues become weak, the scarpus fascia bulges upward, causing the characteristic uneven, dimpled appearance of the skin.

Most procedures are ineffective in removing cellulite except for long term dieting and exercise. The development of cellulite is genetically driven and is considered a normal condition and is thus difficult to remove.

Excessive fat depositions or "lipodystrophies" are produced by a disproportionate increase in the deeper section of the subcutaneous cellular tissues of fat cells. Lipodystrophies are, in part, genetically regulated. Each adipose cell has beta 1 (lipogenic) and alpha 2 (lipolitic) receptors in its membrane. In areas of increased beta 1 receptors a localized lipodystrophy is produced. Some families express increased levels of beta receptors giving rise to enlarged body parts, such as legs, breasts, waist. In these patients, treatment with low caloric diets exclusively is generally unsuccessful. The most effective way to treat cellulite is to directly treat the genetically altered fat tissues and similar tissues in the area of treatment.

Historically, different methods have been developed to treat cellulite, including liposuction and liposculpture. Later ultrasonic liposculpture was developed and there are some reports on "laser liposuction" (using an external laser source), but laser assisted liposuction has not yet been clearly proven to be effective.

U.S. Pat. No. 6,206,873 by Paolini, et al., titled, "Device and Method for Eliminating Adipose Layers by Means of Laser Energy," discloses a hollow needle with an optical fiber in the center. The fat tissue, i.e., adipose cells, is liquefied when the cell membranes degenerate. The fluid is removed by suction through the needle. The laser is used to simply thermally degrade the cell membranes. The reported laser wavelength range is from 0.75 to 2.5 microns, with a preferred wavelength of 1.06 microns. A rounded optical fiber end is shown in FIG. 3 of Paolini, beyond the needle end. Paolini et al. use a Nd:YAG type of laser with wavelengths from 0.75 to 2.5 microns, and further note that the liquid produced may be removed from the body by normal absorption.

In U.S. Pat. No. 6,605,080, Altshuler et al. disclose the removal of lipid rich tissue using an external laser, a YAG source, as well as other lasers whose output energy is in a wavelength range of 880 to 935 nm, 1150 to 1230 nm or 2280 to 2360 nm. It is noted that the radiation in the lower bands, specifically, 900 to 930, and 1150 to 1230, are preferred in the treatment of fat tissue. Specifically, wavelengths near water/OH absorptions are identified as not preferred. The use of a cooling system is recommended.

U.S. Pat. No. 6,743,215 by Bernakei, titled, "Method and Apparatus for Skin Absorption Enhancement and Cellulite Reduction" discloses a process including the application of a compound upon an abraded skin surface followed by electrical and mechanical removal of cellulite.

Publication WO 99/48474 by A. Casale, entitled, "Pharmaceutical or Cosmetic Compositions Containing Photosensitizer Substances," discloses a photosensitizer formulation of liposomes with the photosensitizer substance activated by light of a wavelength between 700 and 900 nm. This publication describes an effective formulation of photosensitizer agent for use in pharmaceutical and cosmetic applications.

Most of the methods mentioned above are useful for fat reduction (overweight or obesity), while cellulite is a different condition related to fat cells which cannot be addressed effectively using the above methods. Presently there is no truly effective treatment for cellulite. There is thus a need for treatment techniques that minimize surface distortion and post operative complications, and remove or reduce cellulite from selected areas. The present invention satisfies this need.

SUMMARY OF THE INVENTION

It is an objective of the present invention to provide a method of cosmetic treatment using laser, LED or other (e.g.

a filtered lamp) radiation in conjunction with a photosensitive drug for the destruction of cellulite tissue in the area of treatment.

It is another objective of the present invention to provide a method of cosmetic treatment using radiation and a photosensitive drug that directly affects the sub-dermal fatty tissues.

It is yet another objective of the present invention to provide a method of cosmetic treatment using PhotoDynamic Therapy (PDT) to directly affect adipose cells causing emulsification of the fatty tissue and then elimination by absorption, removal by the lymphatic system and by drainage.

It is still another objective of the present invention to provide a method of cosmetic treatment using PDT to directly affect the fatty tissues without destruction of the structural tissues.

It is a further objective of the present invention to provide a photosensitizer mixture to be used in a method of cosmetic treatment using PDT to reduce cellulite.

Briefly stated, the present invention provides methods of treating cellulite by means of a percutaneous application into the area of cellulite buildup followed by light illumination. The photosensitizer can be combined with one or more cellular products including adipose cells and/or collagen that have been previously removed by liposuction. The cosmetic treatment method substantially reduces or removes localized lipodystrophies and/or flaccidity and/or cellulite by localized laser, LED, or other light irradiation of the area of treatment containing a photosensitizer, while minimizing trauma.

The above, and other objectives, features and advantages of the present invention will become apparent from the following description read in conjunction with the accompanying drawings.

BRIEF DESCRIPTION OF THE DRAWINGS

FIGS. 6A and B illustrate marking of sectors of the leg and buttocks having cellulite.

DETAILED DESCRIPTION OF THE INVENTION

Many women suffer, have suffered or will at some time be afflicted with cellulite. It is an aesthetic condition that only has general pathological connotations. It is more common in women, in general, particularly women older than 20 years.

The appearance of cellulite is a psychologically depressing event to many women, because it appears in body areas that are exposed when wearing bathing suits, for example. The skin has a bubbly appearance with depressions and hills.

Millions of dollars are spent by women seeking a cure each year for advertised remedies by the cosmetology industry. Many of these remedies do not provide long term solutions but only temporary relief by the elimination of excess water from cellular tissues. There is not an adequate definitive solution for cellulite, just medical and cosmetologic treatments that generally do not provide complete satisfaction.

The goals of the present invention in regards to the treatment of cellulite are to (1) provide a method of aesthetic alterations of the skin for improving its appearance; (2) provide a process for homeostasis of the cells that are altered in the treatment of cellulite; and (3) increase the web of collagen for optimizing the results of the adipose graft when treating cellulite.

In the present invention, suitable photosensitizer porphyrins and their derivatives, including, but not limited to, temoporfin, chlorins, bacteriopheophorbide, bacteriochlorins are used. The selected photosensitizer can be administered using suitable delivery systems such as liposomes, prodrugs, etc. for efficient drug delivery to selected target cells. As used herein, 'photosensitize' includes precursors of photosensitizers, which are naturally converted to photosensitizers after introduction into a patient as a precursor.

Figure 1:
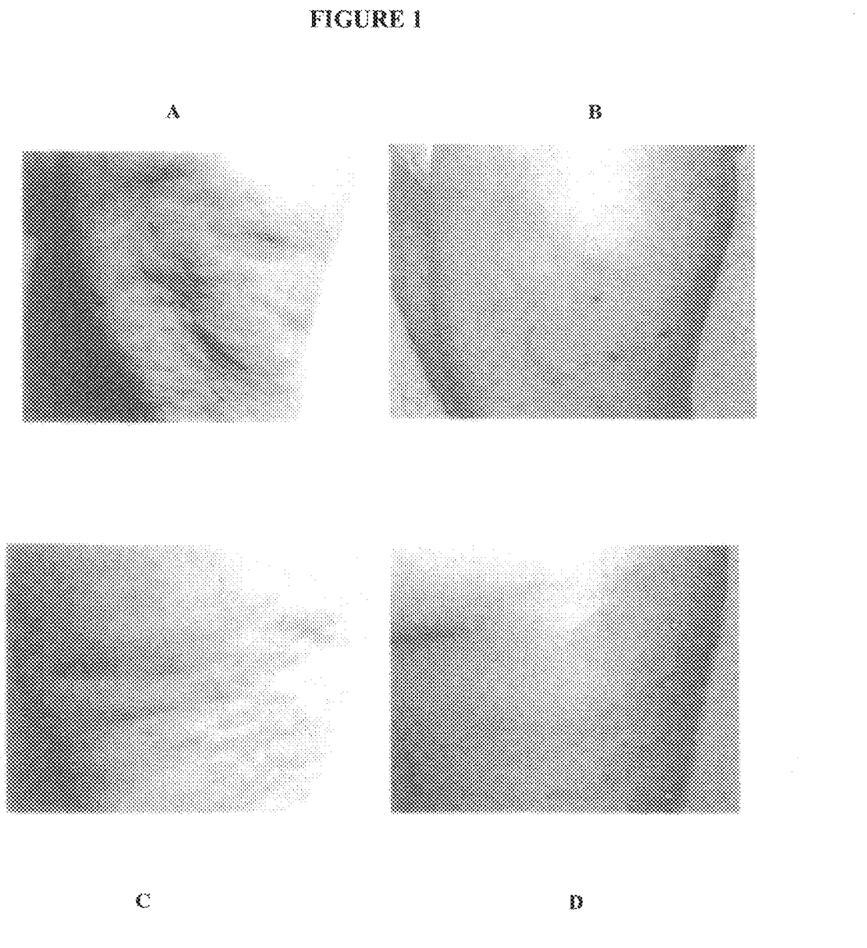
FIG. 1 illustrates the appearance before (A) and a few days after (B) treatment of cellulite in a hip area and before (C) and a few days after (D) treatment of cellulite in a lower buttock area of the same patient.
Figure 2:
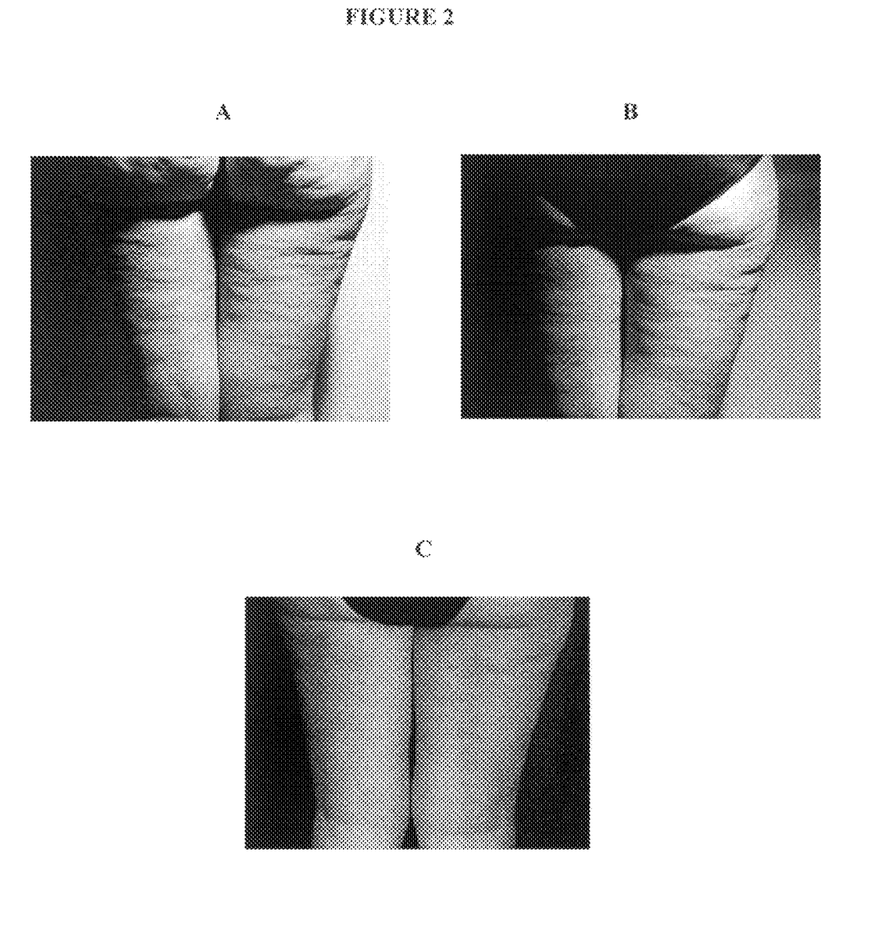
FIG. 2 illustrates the effects of treatment on another patient. (A) Before treatment, (B) one month after treatment, (C) six months after treatment.

FIGS. 1 and 2 present dramatic evidence of the success of the present invention in substantially reducing the effects and appearance of cellulite in two patients after only 1 or several treatments and only a few days after the treatments.

When the photosensitizer, temoporfin, is activated with light from a diode laser, e.g., 652 nm wavelength, this produces an intracellular oxidation that is believed to modify cell membrane properties, the cytoplasm, ribosomes, Golgi apparatus, and nucleus, eventually triggering a series of events that result in apoptosis.

When exposed to the effects of temoporfin or other photosensitizer, the cell begins a series of morphological changes. The plasma membrane appears altered and characteristic blebbing appears. Cell volume decreases considerably and the cytoplasm condenses. The nucleus becomes smaller and chromatin becomes denser and eventually collapses, splitting into several spheres of material.

At the end of apoptosis, the cell is ingested by phagocytosis, avoiding the typical inflammatory response of normal cell necrosis. Even though the cell disappears, there is an increase in the collagen web. This improves the support of collagen and realignment of the collagen fibers and elastin, decreases the gelatinous consistency of the fundamental inter-cell substance, improves oxygenation and cell nutrition, and decreases retention of toxic metabolites and edema.

Figure 3:
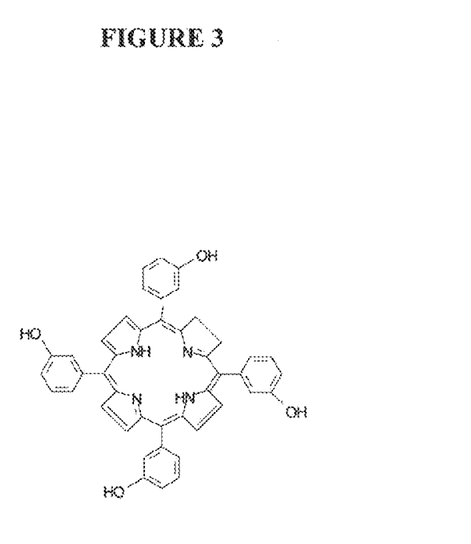
FIG. 3 shows the chemical structure of Temoporfin, 3,3',3'',3'''-(2,3-dihydroporphyrin-5,10,15,20-tetrayl)tetraphenol, also known as m-THPC.
Figure 4:
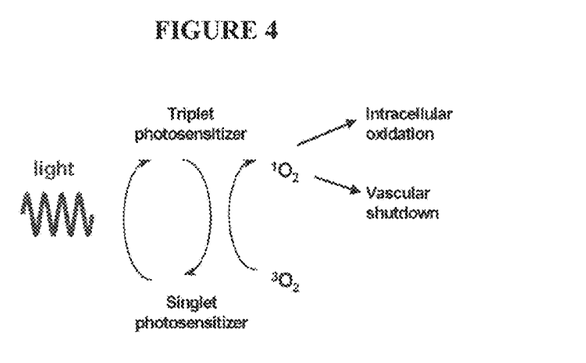
FIG. 4 illustrates the effects of photoactivation of temoporfin on cells

Temoporfin is a very efficient generator of active oxygen which does not require a large dose of the drug or a long exposure to light. Temoporfin is totally innocuous and inactive in the dark, is activated with low intensities of light, and turns into a powerful isolated-oxygen generator. In the past, temoporfin has been used to treat head and neck cancers. FIG. 3 shows the structure of temoporfin and FIG. 4 illustrates temoporfin's effects upon activation. Intracellular oxidation is responsible for alteration of the membrane surface and intracellular changes resulting in apoptosis.

EXAMPLES

Example 1

General Procedure

A patient having cellulite is treated with temoporfin in several sessions. The variables in this treatment program are as follows:

1. Determination of the grade of cellulite in the patient;
2. Determination of the dose and concentration of temporfin, confirmation that it produces an improvement on the cellulite, and ensuring that it is possible to apply it directly by mesotherapy without the need of systemic introduction;
3. Determination of the potency of temoporfin based on the time of application to the time of laser application; and
4. Determination as to accompanying treatments.

The dilutions used for treatment are presented in Table 1.

TABLE 1

| PRODUCT | PURE TEMOPORFIN | PHYSIOLOGICAL SERUM | CONCENTRATION mg/ml |
|---|---|---|---|
| 5 gr. | 7.5 mg | 5 ml | 1.5 mg/ml |
| 5 gr. | 7.5 mg | 25 ml | 0.3 mg/ml |
| 5 gr. | 7.5 mg | 37.5 ml | 0.2 mg/ml |
| 5 gr | 7.5 mg | 50 ml | 0.15 mg/ml |
| 5 gr | 7.5 mg | 75 ml | 0.1 mg/ml |

To treat cellulite, a concentration of 0.005 mg/ml is applied directly by mesotherapy. This concentration results from the study of optimal concentrations for the use of m-THPC on the treatment of tumors, i.e., 0.1 to 0.3 micrograms per gram of tumor tissue. The aesthetic doses are 10 times lower for cellulite treatment as the objective is to develop a collagen matrix and not destroy a tumor. Therefore, the aesthetic doses range from 5 to 15 µg/50 g of cellulite tissue.

To apply mesotherapy on 50 g of tissue, 2 cc of temoporfin solution is applied (area of 100 cm$^2$ with a diffusion of 0.5 cm depth).

The 2 cc of mesotherapy solution must contain 0.005 to 0.015 mg of m-THPC, so the concentration of m-THPC for mesotherapy on cellulite will be 0.005 mg/ml to 0.01 mg/ml.

General Procedure:

In order to determine the stage of cellulite as well as the location of the cellulite in the patient, contact thermography may be used. High Resolution Contact Thermography is ideal for classification of the grade of cellulite and for tracking cellulite during treatment, since small variations are evidenced during treatment. This process measures the superficial temperature of the skin surface. A plate of capsulated liquid crystals is placed in contact with the skin. The color of the crystals is an indication of the temperature of the underlying skin. Several plates are available having different temperature ranges appropriate for skin application. Two of these plates are shown in FIG. 5A.

Figure 5:
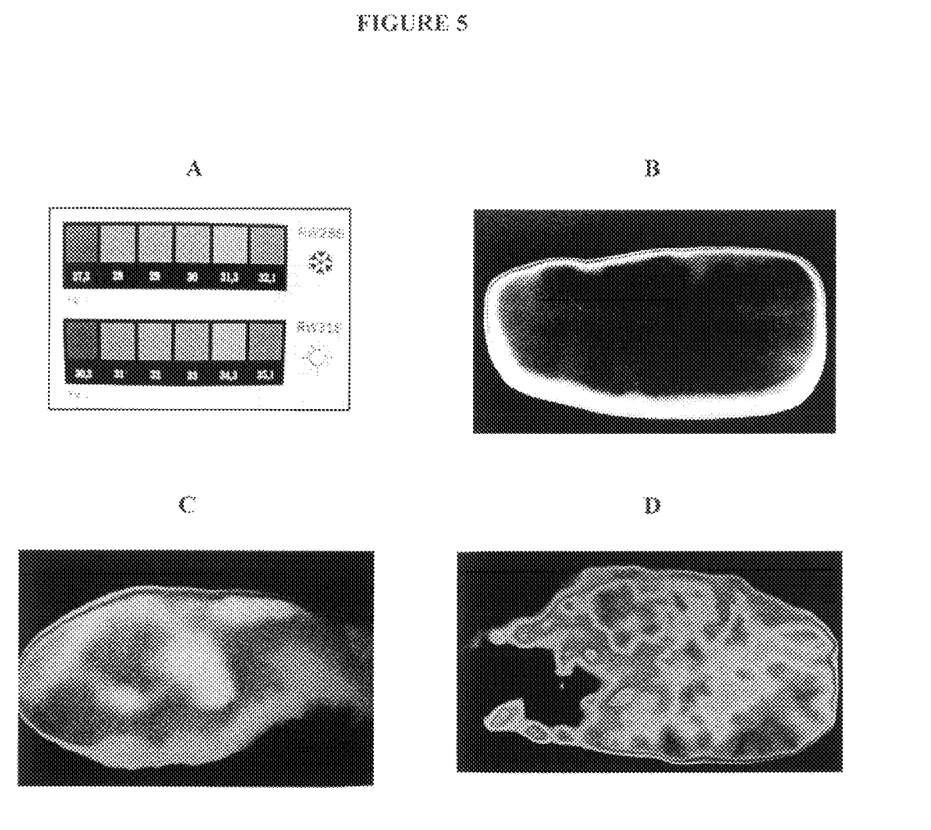
FIG. 5 illustrates the use of high resolution contact thermography to classify cellulite. (A) Color plates for determining temperature of the hypodermis, (B) Thermography of normal tissue having no cellulite, (C) Thermography of stages I and II cellulite, (D) Thermography of stage IV cellulite.

The brown colors mark hypothermic zones with little circulation and the blue colors indicate hypothermic zones with increased circulation. The temperatures are registered on the skin and provide 3 or 4 grades of temperatures of the hypodermis. The homogeneous imagery indicates the condition of the cellulite and provides precise diagnosis, topography and cellulite staging, as shown in FIGS. 5B-D. FIG. 5 B shows a uniform, unstained color image that is obtained in areas with no cellulite. A reference thermography may be performed on the patient's arm or forearm, which are zones that, in general, do not present cellulite.

FIGS. 5C and D illustrates Stage I and II cellulite. The following conditions are indicative of Stages I and II: Slowing of the venous and lymphatic circulation with the dilatation of the small veins of the deep cape of the dermis, Interstitial edema at zones surrounding the adipose cells, rapid increase in exudation of serum from capillaries of the subcutaneous tissue. The zone with edema compresses the conjunctive fibers as well as the nerve elements, and may be manifested by spontaneous pain or pain upon touch. There may be alterations in sensitivity and formation of stretch marks. Histological examination reveals hyperplasia and hypertrophy of the reticular fibers that surround adipose cells and capillaries. These phases are reversible.

Thermography in these stages shows large and diffuse hyperthermic borders, surrounding hypothermic diffuse zones and the image shows the alteration and instability of the microcirculation of the zone.

In Stage III, there is fibrous proliferation. The fibers swell and there is a decrease in collagen, an increase in fibrin, and loss of the individual characteristics of small fibers that mask a named fibrinoid type. Collagen is deconstructed and degenerated, forming irregular, amorphous blocks. The clinical and visual appearance is termed "orange skin." There is retardation of vascular interchanges resulting in the formation of micronodules. In this phase, reversal of skin alterations is difficult.

FIG. 5D shows a multi-colored image where the predominate colors are celestial green and pink. The skin has a "leopard" appearance, localizing irregularities of temperature caused by micronodules. The very cold zones indicated by black begin to appear as "black holes" which characterize stage IV cellulite. In stage IV, the fibrosis increases and compresses veins and nerves, producing changes in the connective tissue. The adipose tissue is divided into compartments like tablets with large hypothermic blocks caused by low blood circulation. The adipocytes are normal, but compressed. Several contiguous intervening micronodules fuse into one capsule, forming a macronodule that is palpable. Clinically the skin presents a padded appearance with painful, isolated macronodules or hard plates. In this stage flabbiness is observed. Thermographically, the image shows black holes with extensive hypothermic zones that indicate the presence of macronodules.

In this example, the patient is administered the temoporfin solution as follows: In all sequences, the treatment consists of only one session per area to be treated, and, if necessary, it is repeated in 30 days. In general, it was observed that only one session, followed by appropriate physiotherapy, such as ultrasound, lymph-drainage, thermotherapy, isotonic and isometric electro-stimulation, was usually sufficient in more than 80% of the patients. Table 2 presents further information as to the stage of cellulite, concentration of m-THPC (temoporfin), dose, surface area being treated; strength, power level and time of laser radiation application.

TABLE 2

Parameters for photodynamic therapy treatment of cellulite

| CELLULITE | M-THPC | DOSE | SURFACE | LATENCY | Watts | TIME PDT |
|---|---|---|---|---|---|---|
| I HARROW I II | 0.1 mg/ml | 10 cc | 600 cm2 (20 × 30) | 30' | 2 W | 2' each 100 cm2 |
| I HARROW III | 0.2 mg/ml | 10 cc | 600 cm2 (20 × 30) | 30' | 2 W | 2' each 100 cm2 |
| I HARROW IV | 0.2 mg/ml | 10 cc | 400 cm2 (20 × 20) | 30' | 2.5 W | 3' each 100 cm2 |

Figure 6:
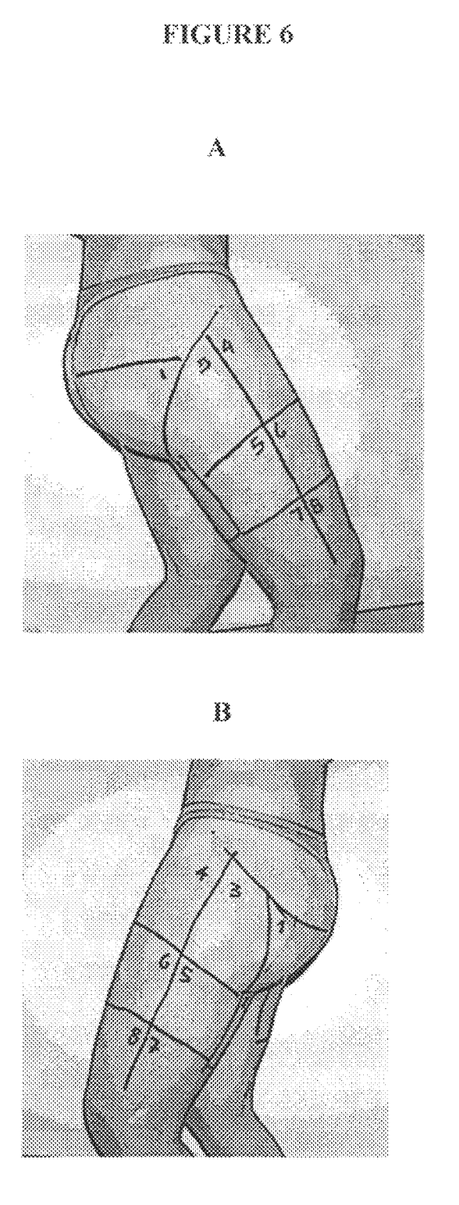

The parameters shown in Table 2 may be adjusted depending on the patient's condition. The following is a listing of the sequence of events in each session:

1. Prepare a map with sectorial thermographic images, as shown in FIG. 6, and record this information for each patient for reference during treatment;
2. Identify zones on the patient's body for areas of treatment;
3. Disinfect skin with alcohol;
4. Apply the temoporfin solution in accordance with the treatment plan established;
5. Apply ultrasound at the rate of 1 minute for each 100 cm² of treated surface to distribute the temoporfin within the cellulite tissue and wait for 30 minutes;
6. Apply laser radiation at a height of about 6.25 to 2.5 cm from the skin surface, using a spot of 3 cm in a continuous mode, with a potency of 2 watts, for 2 or 3 minutes on each 100 cm². Procedure may be adapted depending on grade of cellulite and applied dose of temoporfin;
7. Apply a cold gel covered by plastic film to the areas of treatment and leave on skin for 2 hours;
8. Allow the patient to remove the cold gel with a natural sponge applied in circles.

The results of the treatment should be followed by thermography noting cold zones, micro-nodules and black holes. The patient's body should be mapped as sectors, e.g., gluteus, posterior of thigh, anterior of thigh, with the cellulite stage level noted for each sector, e.g., as in FIG. 6. This is beneficial for follow-up treatments and consultations. Because of the low dose concentration of temoporfin, the cost should be low so that it will be affordable. In addition, LIPOFUNDIN MCT® 10% may be applied in the tissue containing cellulite to improve diffusion of the temoporfin. Lipofundin may also be used to dilute the temoporfin solution.

Example 2

Special Treatments

Temoporfin is a photosensitizer having affinity for phospholipids and cell membranes, but is not soluble in triglycerides. The appearance of cellulite in the more severe stages is a bubbling affect having depressed areas and hill like areas. These areas may require special treatment as follows:

For Filling Depressed Areas:
1. Prepare diluted temoporfin (formulated in a liposome) at 0.3 mg per ml;
2. Wash and mix five parts fat from liposuction with one part diluted temoporfin;
3. Inject the mixture in the depressed area with an 18 gauge needle;
4. Wait 30 minutes after injection;
5. Apply PDT treatment; and
6. Wash the treated area.

For Elevated Zones or Hills
1. Prepare temoporfin (formulated in a liposome) to 0.3 mg per ml;
2. Inject the diluted temoporfin into the area to be treated;
3. Wait 30 minutes; and
4. Apply PDT treatment.

In summary the general procedure is 1. analysis and marking of areas to be treated; 2. adding photosensitizer solution to areas to be treated, after applying local anaesthetic; 3. lasing of tissue within each area of treatment; 4. squeezing and suctioning of melted fat; and 5. application of ointments, etc. after treatment.

Example 3

Steps for Patient Assessment and Treatment for Localized Cellulite

1. Diagnostic: Clinical evaluation with anthropometric measurements, weight and pictures complemented by the use of thermograph charts to confirm the clinical assessment of the cellulite stage (I, II, III or IV).
2. Treatment:
    a. Temoporfin (formulated in a liposome) mesotherapy deep injection:
        i. 2 cc/100 cm² of area to be treated with one injection of 0.05 mg/ml temoporfin dilution (Stage IV); and
        ii. 2 cc/100 cm² of area to be treated with one injection of 0.025 mg/ml temoporfin dilution (Stage II and III).

For example, on a buttock area of treatment, 6 or 8 cc of solution is used with 0.05 or 0.025 mg/ml temoporfin depending on the stage of cellulite. For serious conditions, liposuction is used to obtain some of the patient's own fat, which is cleaned and then injected into the depressed areas;
    b. Lymph-drainage or soft massage to distribute the drug within the area of treatment;
    c. Wait 30 minutes;
    d. Laser illumination: area is divided into spots to cover the whole area and a fluence of 0.8 J/cm2 is used on stage II & III cellulite (with 0.5 W and time according to the area) or 1 J/cm2 for stage IV cellulite (with 0.75 W).
3) Immediate post-treatment:
    a. Gel application; and
    b. Light compression stockings.
4) 48 h post-treatment: complementary sessions such as lymph-drainage, press therapy, ultrasound, gels, etc. may be applied.
5) Follow-up: Assessment of results.

Example 4

LED Based PDT for Cellulite Reduction

Before starting the treatment, the patient's clinical history is determined and a physical examination is performed. The cellulite is staged by clinical impression and by thermography.

A liposomal formulation of temoporfin diluted in 5% glucose solution is prepared. A composition containing 1 part liposomal formulation of temoporfin and 9 parts lipofundin, which improves drug diffusion into the cellulite, is prepared.

A pistol-like device with a trigger is used to inject the composition into the treatment site. Two injections are made to deliver 12 ul of the temoporfin composition to a depth of 0.5 cm. Injection sites are separated by about 0.5 cm. Dose of the drug can be increased based on the stage of cellulite to be treated.

Illumination is performed using LED arrays (area of the array is 4×4 cm) with wavelength of 652 nm and power density of 180 mW/cm².

Treatment schedule: Four LED treatments are performed on the patient. The first begins 48 h after injection of the liposomal formulation of temoporfin. The second, third and fourth treatments are performed 7, 14 and 21 days after temoporfin injection.

The patient is examined at the end of 21 days. Subsequent examination generally shows improvement with better skin texture resulting in smoother skin.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A cosmetic method of reducing unwanted cellulite in selective areas of a person comprising the steps of:
    (a) identifying said selective areas to be treated;
    (b) mixing at least one photosensitizer with a product previously removed from said person by liposuction wherein said product is selected from the group consisting of adipose cells, collagen, hyaluronic acid and a mixture of adipose cells and collagen to form a treatment fluid;
    (c) administering said treatment fluid to said person in said selective areas;
    (d) allowing a sufficient time for said photosensitizer to accumulate in cellulite of said selective areas of treatment; and
    (e) selectively activating by light said photosensitizer in said selective areas to reduce or eliminate cellulite.

2. The cosmetic method of reducing unwanted cellulite according to claim 1, wherein said photosensitizer is Temoporfin.

3. The cosmetic method of reducing unwanted cellulite according to claim 1, wherein said product is adipose cells.

4. The cosmetic method of reducing unwanted cellulite according to claim 3, wherein the ratio of said photosensitizer and said product in said treatment fluid is about 1 part to 5 parts by volume.

5. The cosmetic method of reducing unwanted cellulite according to claim 1 wherein a volume of said treatment fluid administered to said selective area is adjusted according to whether said cellulite is in a depressed area of the skin, or an elevated area on the skin.

6. The cosmetic method of reducing unwanted cellulite according to claim 1 wherein said administering step is by local application to the areas to be treated.

7. The cosmetic method of reducing unwanted cellulite according to claim 1 wherein said selectively activating is by means of electromagnetic radiation, wherein said electromagnetic radiation includes a wavelength matching at least one peak within said photosensitizer's absorption spectrum., and wherein said electromagnetic radiation is emitted by a light source selected from the group consisting of diode lasers, LEDs, and one or more lamps with filters.

8. The cosmetic method of reducing unwanted cellulite according to claim 7 wherein said radiation is applied by means of at least one optical fiber.

9. The cosmetic method of reducing unwanted cellulite according to claim 8 wherein said optical fiber has an output tip having a diffusing device thereon.

10. The cosmetic method of reducing unwanted cellulite according to claim 1 wherein said cellulite is adipose tissue accumulated in pockets under the skin of said organism forming depressed and elevated areas.

11. The cosmetic method of reducing unwanted cellulite according to claim 10 wherein adipose tissue is white adipose tissue.

12. The cosmetic method of reducing unwanted cellulite according to claim 1 wherein said identifying step comprises determining the stage of cellulite by thermography.

* * * * *